(12) United States Patent
Kim

(10) Patent No.: US 10,898,163 B2
(45) Date of Patent: Jan. 26, 2021

(54) ULTRASOUND IMAGING APPARATUS AND METHOD OF OPERATING THE SAME

(71) Applicant: SAMSUNG MEDISON CO., LTD., Hongcheon-gun (KR)

(72) Inventor: Deok-gon Kim, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 428 days.

(21) Appl. No.: 15/347,914

(22) Filed: Nov. 10, 2016

(65) Prior Publication Data

US 2017/0128040 A1 May 11, 2017

Related U.S. Application Data

(60) Provisional application No. 62/253,230, filed on Nov. 10, 2015.

(30) Foreign Application Priority Data

Sep. 21, 2016 (KR) .................. 10-2016-0120753

(51) Int. Cl.
*A61B 8/06* (2006.01)
*A61B 8/08* (2006.01)
(Continued)

(52) U.S. Cl.
CPC .............. *A61B 8/14* (2013.01); *A61B 8/06* (2013.01); *A61B 8/0883* (2013.01); *A61B 8/463* (2013.01); *A61B 8/469* (2013.01); *A61B 8/488* (2013.01); *A61B 8/5207* (2013.01); *A61B 8/5223* (2013.01); *A61B 8/5246* (2013.01);
(Continued)

(58) Field of Classification Search
CPC ....... A61B 8/14; A61B 8/5253; A61B 8/5246; A61B 8/463; A61B 8/0883; A61B 8/5223; A61B 8/5207; A61B 8/469; A61B 8/488; A61B 8/06-065; G01S 15/8981; G01S 15/8988; G01S 7/52025; G01S 7/52034; G01S 7/52084
See application file for complete search history.

(56) References Cited

U.S. PATENT DOCUMENTS 5,685,308 A * 11/1997 Wright ................ G01S 7/52023
600/443
5,961,462 A 10/1999 Loupas et al.
(Continued)

FOREIGN PATENT DOCUMENTS

CN 101849842 A 10/2010
CN 104127207 A 11/2014
(Continued)

OTHER PUBLICATIONS

Communication dated Mar. 29, 2017, issued by the European Patent Office in counterpart European Application No. 16198027.1.
(Continued)

*Primary Examiner* — Angela M Hoffa
(74) *Attorney, Agent, or Firm* — Sughrue Mion, PLLC

(57) ABSTRACT

Provided are an ultrasound imaging apparatus and a method of operating the same. The ultrasound imaging apparatus may generate a plurality of color Doppler mode images by extracting a plurality of pieces of ensemble data from among ultrasound data acquired from the object.

15 Claims, 12 Drawing Sheets

(51) Int. Cl.
  *G01S 15/89* (2006.01)
  *A61B 8/14* (2006.01)
  *G01S 7/52* (2006.01)
  *A61B 8/00* (2006.01)

(52) U.S. Cl.
  CPC ........ *A61B 8/5253* (2013.01); *G01S 7/52025* (2013.01); *G01S 7/52034* (2013.01); *G01S 15/8981* (2013.01); *G01S 15/8988* (2013.01); *G01S 7/52084* (2013.01)

(56) References Cited

U.S. PATENT DOCUMENTS

| | | | |
|---|---|---|---|
| 6,139,501 A | 10/2000 | Roundhill et al. | |
| 6,450,959 B1 | 9/2002 | Mo et al. | |
| 8,666,132 B2* | 3/2014 | Takeshima | H04N 19/124 |
| | | | 382/128 |
| 8,684,933 B2* | 4/2014 | Hao | G01S 15/8988 |
| | | | 600/441 |
| 9,420,997 B2* | 8/2016 | Wong | A61B 8/5223 |
| 9,474,510 B2 | 10/2016 | Kim et al. | |
| 9,592,032 B2* | 3/2017 | Rothberg | A61B 8/4494 |
| 10,575,825 B2* | 3/2020 | Freiburger | A61B 8/461 |
| 2001/0009977 A1* | 7/2001 | Sato | A61B 8/06 |
| | | | 600/441 |
| 2009/0131791 A1 | 5/2009 | Clark | |
| 2011/0295116 A1* | 12/2011 | Lee | G01S 7/52088 |
| | | | 600/437 |
| 2012/0046548 A1* | 2/2012 | Hao | A61B 8/14 |
| | | | 600/440 |
| 2012/0184856 A1* | 7/2012 | Dasgupta | A61B 8/06 |
| | | | 600/454 |
| 2012/0232399 A1* | 9/2012 | Lee | G01S 7/52046 |
| | | | 600/453 |
| 2013/0165784 A1 | 6/2013 | Kim et al. | |
| 2013/0165792 A1* | 6/2013 | Lee | G01S 15/8984 |
| | | | 600/453 |
| 2013/0172749 A1* | 7/2013 | Lee | G01S 7/52034 |
| | | | 600/443 |
| 2013/0182926 A1* | 7/2013 | Lee | G06K 9/00671 |
| | | | 382/131 |
| 2013/0245441 A1* | 9/2013 | Datta | A61B 8/13 |
| | | | 600/438 |
| 2014/0018680 A1 | 1/2014 | Guracar | |
| 2014/0046606 A1* | 2/2014 | Torp | A61B 8/463 |
| | | | 702/54 |
| 2018/0220997 A1* | 8/2018 | Song | G01S 15/8981 |

FOREIGN PATENT DOCUMENTS

| | | |
|---|---|---|
| JP | 6-269453 A | 9/1994 |
| JP | 4276532 B2 | 6/2009 |
| JP | 4723712 B2 | 7/2011 |
| KR | 10-1406806 B1 | 6/2014 |

OTHER PUBLICATIONS

Communication dated May 22, 2020 issued by the State Intellectual Property Office of P.R. China in counterpart Chinese Application No. 201610997142.9.

* cited by examiner

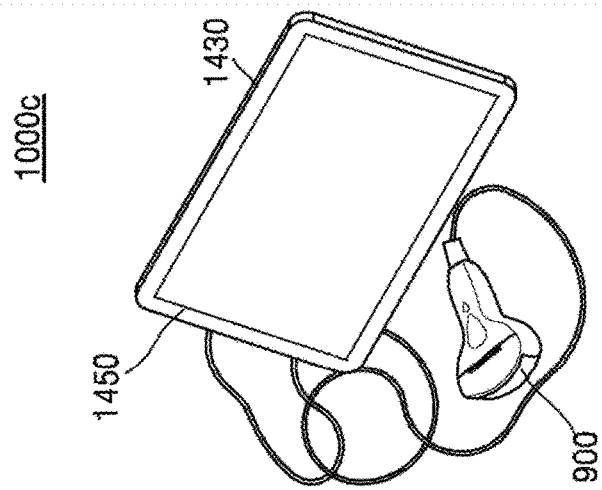
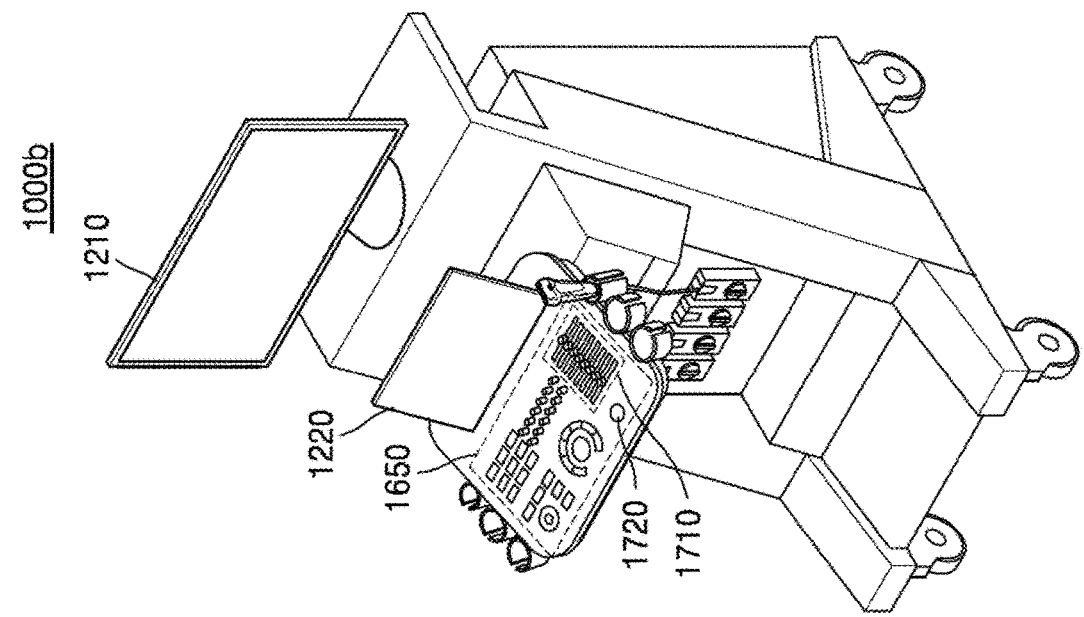
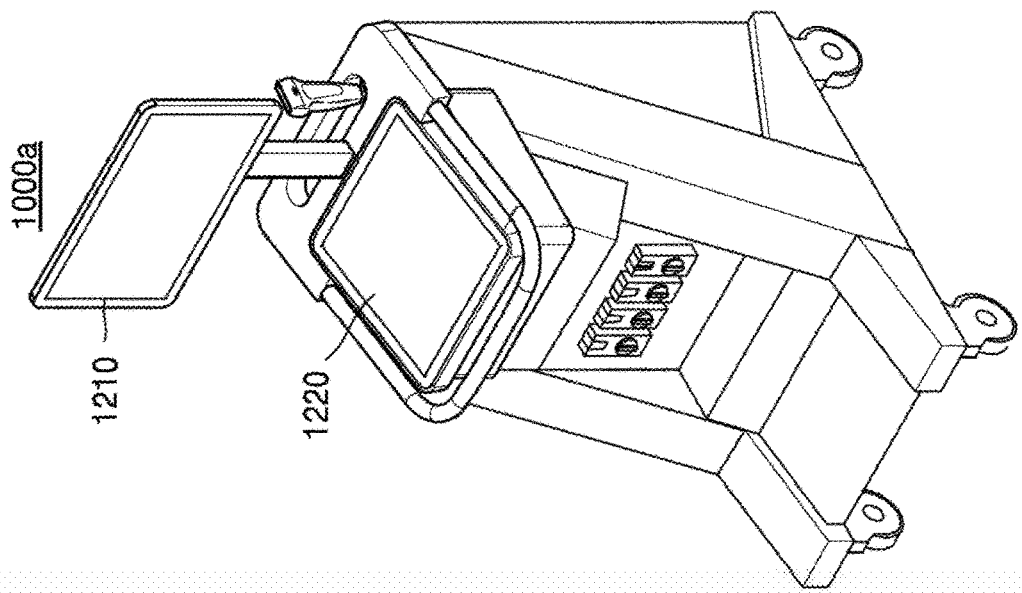

ULTRASOUND IMAGING APPARATUS AND METHOD OF OPERATING THE SAME

CROSS-REFERENCE TO RELATED APPLICATIONS

This application claims the benefit of U.S. Provisional Patent Application No. 62/253,230, filed on Nov. 10, 2015, in the U.S. Patent and Trademark Office, and the benefit of Korean Patent Application No. 10-2016-0120753, filed on Sep. 21, 2016, in the Korean Intellectual Property Office, the disclosures of which are incorporated herein in their entireties by reference.

BACKGROUND

1. Field

The present disclosure relates to ultrasound imaging apparatuses and methods of operating the same, and more particularly, to ultrasound imaging apparatuses and methods of generating a plurality of color Doppler mode images based on acquired ultrasound data and displaying the generated color Doppler mode images.

2. Description of the Related Art

Due to its non-invasive and non-destructive nature, an ultrasound imaging apparatus has become widely used in many medical fields that require information about the inside of an object. The ultrasound imaging apparatus also plays a critical role in medical diagnosis since it can provide high-resolution images of an inner area of an object to a medical practitioner without the need for performing a surgical procedure to directly incise the object for observation.

An ultrasound imaging apparatus provides a brightness (B) mode image visualizing reflection coefficients of ultrasound signals (i.e., ultrasound echo signals) reflected from an object as a two-dimensional (2D) image, a Doppler (D) spectrum image showing a velocity of a moving object in the form of a Doppler spectrum by using a Doppler effect, a color Doppler mode image showing a velocity and a direction of a moving object in colors by using a Doppler effect, an elasticity image visualizing a difference between responses when compression is or is not applied to an object as an image, etc.

In particular, an ultrasound imaging apparatus transmits ultrasound signals to a living body at intervals of a pulse repetition frequency (PRF) and receives ultrasound echo signals reflected from the living body to acquire ultrasound data corresponding to an ultrasound image. The ultrasound data is then stored in a memory. The ultrasound imaging apparatus may generate an ultrasound image based on the ultrasound data stored in the memory.

SUMMARY

Provided are ultrasound imaging apparatuses and methods of operating the same, whereby movement of and changes in blood flow may be easily displayed by extracting a plurality of pieces of ensemble data from among ultrasound data acquired from an object and generating a plurality of color Doppler mode images based on the extracted plurality of pieces of ensemble data.

Additional aspects will be set forth in part in the description which follows and, in part, will be apparent from the description, or may be learned by practice of the presented embodiments.

According to an aspect of an embodiment, an ultrasound imaging apparatus for generating an ultrasound Doppler image of a region of interest (ROI) of an object includes: an ultrasound data acquisitor configured to transmit ultrasound signals to the object at intervals of a pulse repetition frequency (PRF), receive ultrasound echo signals reflected from the object, and acquire a first ensemble number of ensemble data by focusing and demodulating the ultrasound echo signals; a memory configured to store the acquired first ensemble number of ensemble data; a processor configured to selectively extract a second ensemble number of ensemble data from among the stored first ensemble number of ensemble data to thereby generate a plurality of ensemble data sets and generate a plurality of frames of color Doppler mode images respectively based on the plurality of ensemble data sets; and a display configured to display the plurality of frames of color Doppler mode images.

The processor may be further configured to sequentially extract the second ensemble number of ensemble data in an overlapping manner while skipping extraction of at least one ensemble data from among the first ensemble number of ensemble data stored in the memory.

The second ensemble number may be less than or equal to the first ensemble number.

The second ensemble number may be greater than or equal to two (2).

The processor may be further configured to select and extract each of the stored first ensemble number of ensemble data at least once.

The processor may be further configured to perform clutter filtering on the acquired first ensemble number of ensemble data before storing the first ensemble number of ensemble data in the memory, and the memory may be further configured to store the first ensemble number of ensemble data that have undergone the clutter filtering.

The processor may be further configured to perform, after generating the plurality of ensemble data sets, clutter filtering on the ensemble data in the plurality of ensemble data sets to thereby produce Doppler data, calculate velocity components and power components of the Doppler data, and generate the plurality of frames of color Doppler mode images based on the calculated velocity components and power components, and the ensemble data may include In-phase-Quadrature (IQ) data.

For example, the processor may create the Doppler data before generating the plurality of ensemble data sets.

The ultrasound data acquisitor may be further configured to acquire radio frequency (RF) data from the ultrasound echo signals, and the processor may be further configured to generate a single frame of a brightness (B) mode image based on the RF data.

The processor may be further configured to arrange the generated plurality of frames of color Doppler mode images at equally spaced intervals along a time axis so that each interval is equal to a frame rate at which each of the plurality of frames of color Doppler mode images is displayed on the display.

According to an aspect of another embodiment, a method of generating an ultrasound Doppler image of an ROI of an object includes: transmitting ultrasound signals to the object at intervals of a pulse repetition frequency (PRF), receiving ultrasound echo signals reflected from the object, and acquiring a first ensemble number of ensemble data by focusing and demodulating the ultrasound echo signals; storing the acquired first ensemble number of ensemble data; selectively extracting a second ensemble number of ensemble data from among the stored first ensemble number of ensemble data to thereby generate a plurality of ensemble data sets; and generating a plurality of frames of color Doppler mode images respectively based on the plurality of ensemble data sets.

The generating of the plurality of ensemble data sets may include sequentially extracting the second ensemble number of ensemble data in an overlapping manner while skipping extraction of at least one ensemble data from among the stored first ensemble number of ensemble data.

The second ensemble number may be less than or equal to the first ensemble number.

The second ensemble number may be greater than or equal to two (2).

Each of the stored first ensemble number of ensemble data may be selected and extracted at least once.

The method may further include performing clutter filtering on the acquired first ensemble number of ensemble data, wherein the storing of the acquired first ensemble number of ensemble data may include storing the first ensemble number of ensemble data that have undergone the clutter filtering.

The method may further include: performing, after the generating of the plurality of ensemble data sets, clutter filtering on the ensemble data in the plurality of ensemble data sets to thereby produce Doppler data; calculating velocity components and power components of the Doppler data; and generating the plurality of frames of color Doppler mode images based on the calculated velocity components and power components, wherein the ensemble data may include In-phase-Quadrature (IQ) data.

The method may further include: acquiring radio frequency (RF) data from the ultrasound echo signals; and generating a single frame of a brightness (B) mode image based on the RF data.

The method may further include: arranging the generated plurality of frames of color Doppler mode images at equally spaced intervals along a time axis so that each interval is equal to a frame rate at which each of the plurality of frames of color Doppler mode images is displayed on a display; and displaying the plurality of frames of color Doppler mode images on the display.

According to an aspect of another embodiment, a non-transitory computer-readable recording medium has recorded thereon a program for executing the above-described method on a computer.

BRIEF DESCRIPTION OF THE DRAWINGS

These and/or other aspects will become apparent and more readily appreciated from the following description of the embodiments, taken in conjunction with the accompanying drawings in which:

FIGS. 13A through 13C illustrate ultrasound imaging apparatuses according to embodiments.

DETAILED DESCRIPTION

Figure 1:
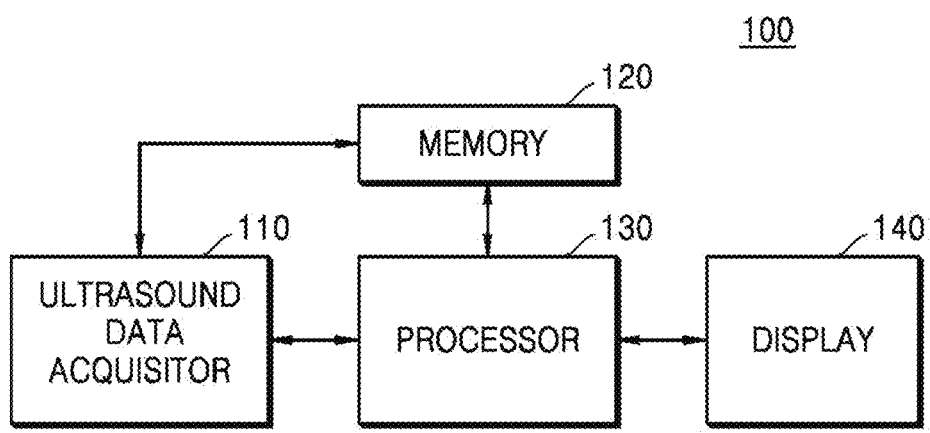
FIG. 1 is a block diagram of a configuration of an ultrasound imaging apparatus according to an embodiment.

The present specification describes principles of the present disclosure and sets forth embodiments thereof to clarify the scope of the present disclosure and to allow those of ordinary skill in the art to implement the embodiments. The present embodiments may have different forms and should not be construed as being limited to the descriptions set forth herein.

Like reference numerals refer to like elements throughout. The present specification does not describe all components in the embodiments, and common knowledge in the art or the same descriptions of the embodiments will be omitted below. The term "part" or "portion" used herein may be implemented using hardware or software, and according to embodiments, a plurality of "parts" or "portions" may be formed as a single unit or element, or one "part" or "portion" may include a plurality of units or elements. Hereinafter, the operating principles and embodiments of the present disclosure will be described in detail with reference to the accompanying drawings.

In the present specification, an "image" may include a medical image obtained by a magnetic resonance imaging (MRI) apparatus, a computed tomography (CT) apparatus, an ultrasound imaging apparatus, an X-ray apparatus, or another medical imaging apparatus.

Furthermore, in the present specification, an "object" may be a target to be imaged and include a human, an animal, or a part of a human or animal. For example, the object may include a body part (an organ, etc.) or a phantom.

Throughout the specification, an "ultrasound image" refers to an image of an object, which is formed by processing ultrasound signals transmitted to and reflected from the object.

Furthermore, in the present specification, the terms "first", "second", "1-1", etc. are used to distinguish one component, element, object, data, image, pixel, or patch from another component, element, object, data, image, pixel, or patch. Thus, these terms are not intended to represent the order or priority among elements or components. Expressions such as "at least one of," when preceding a list of elements, modify the entire list of elements and do not modify the individual elements of the list.

Embodiments will now be described more fully hereinafter with reference to the accompanying drawings so that they may be easily implemented by one of ordinary skill in the art. In addition, parts not related to the present disclosure are omitted to clarify the description of the embodiments.

FIG. 1 is a block diagram of a configuration of an ultrasound imaging apparatus 100 according to an embodiment. The ultrasound imaging apparatus 100 according to the present embodiment may be a cart type apparatus or a portable type apparatus. Examples of portable ultrasound imaging apparatuses may include, but are not limited to, a picture archiving and communication system (PACS) viewer, a smart phone, a laptop computer, a personal digital assistant (PDA), and a tablet personal computer (PC).

Referring to FIG. 1, the ultrasound imaging apparatus 100 includes an ultrasound data acquisitor 110, a memory 120, a processor 130, and a display 140. Throughout the specification, including descriptions with respect to FIG. 1, when a part "includes" or "comprises" an element, unless there is a particular description contrary thereto, the part may further include other elements, not excluding the other elements. Also, the term "unit" used in the specification means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of a program code, drivers, firmware, micro codes, circuits, data, a database, data structures, tables, arrays, or variables. A function provided by the components and "units" may be associated with a smaller number of components and "units", or may be divided into additional components and "units".

Figure 2:
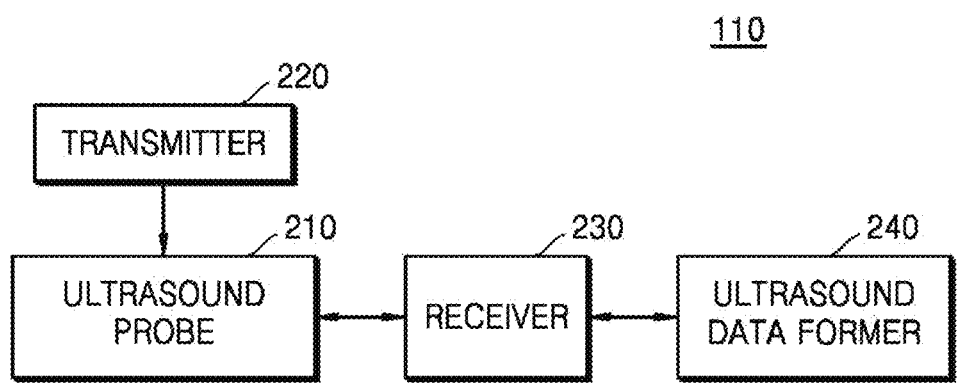
FIG. 2 is a block diagram of a configuration of an ultrasound data acquisitor according to an embodiment.

The ultrasound data acquisitor 110 acquires ultrasound data by transmitting ultrasound signals to a moving object, e.g., an object including blood flow, and receiving ultrasound signals, i.e., ultrasound echo signals reflected from the object. Referring to FIG. 2, the ultrasound data acquisitor 110 may include an ultrasound probe 210, a transmitter 220, a receiver 230, and an ultrasound data former 240. The ultrasound data former 240 will be described in detail below with reference to FIG. 2.

The memory 120 stores ultrasound data acquired by the ultrasound data acquisitor 110. The memory 120 may include at least one of a volatile memory (e.g., dynamic RAM (DRAM), static RAM (SRAM), synchronous dynamic RAM (SDRAM), etc.), a non-volatile memory (e.g., one time programmable ROM (OTPROM), programmable ROM (PROM), erasable and programmable ROM (EPROM), electrically erasable and programmable ROM (EEPROM), mask ROM, flash ROM, etc.), a hard disk drive (HDD), and a solid state drive (SSD). In an embodiment, the memory 120 may include a database.

The memory 120 may store information necessary for distinguishing, from among Doppler signals, blood flow signals resulting from blood flow, clutter signals caused by movement of a vessel wall, etc., and noise based on velocity and power components of the Doppler signals. According to an embodiment, the memory 120 may store an ensemble number of ultrasound data acquired by the ultrasound data acquisitor 110. Furthermore, the memory 120 may store ultrasound data acquired by the ultrasound data acquisitor 110 for each frame corresponding to an ultrasound image. An ensemble number represents the number of times the ultrasound data acquisitor 110 transmits and receives ultrasound signals to and from the object in order to acquire Doppler signals corresponding to one scan line.

The processor 130 is connected to the ultrasound data acquisitor 110 and the memory 120. For example, the processor 130 may be implemented as at least one of a central processing unit (CPU), a graphics processing unit (GPU), and a microprocessor. According to an embodiment, the processor 130 may be implemented using a hardware component such as FPGA or ASIC.

The processor 130 may search the memory 120 and selectively extract ultrasound data necessary for generating an ultrasound image from the memory 120. According to an embodiment, the processor 130 may selectively extract some ultrasound data from among pieces of ultrasound data acquired at intervals of a preset pulse repetition frequency (PRF). In detail, the ultrasound data stored in the memory 120 may include N pieces of ensemble data. In this case, a range of i pieces of ensemble data may be set as a processing ensemble number. Furthermore, the processor 130 may selectively extract, from among a total ensemble number N of ensemble data, consecutively acquired ensemble data corresponding to a processing ensemble number i. The processor 130 may generate a plurality of ensemble data sets by using the extracted processing ensemble number i of ensemble data. In an embodiment, the processor 130 may sequentially extract the processing ensemble number i of ensemble data in an overlapping manner while skipping extraction of one ensemble data from among N pieces of ensemble data stored in the memory 120.

In this case, the processing ensemble number i may be an integer value that is less than the ensemble number N, but is not limited thereto. According to an embodiment, the processing ensemble number i may be equal to the ensemble number N.

In an embodiment, the processor 130 may extract each of the N ensemble number of ensemble data stored in the memory 120 at least once. In other words, ultrasound data stored in the memory 120 may be selected and extracted by the processor 130 in an overlapping manner.

The processor 130 may generate a plurality of frames of ultrasound images, based on a plurality of ensemble data sets generated by using extracted ensemble data. According to an embodiment, the ultrasound data stored in the memory 120 may include radio frequency (RF) data and In-phase-Quadrature (IQ) data. The processor 130 may generate a brightness (B) mode image based on RF data stored in the memory 120. Furthermore, the processor 130 may generate a plurality of frames of color Doppler mode images using IQ data stored in the memory 120.

The display 140 displays a plurality of frames of ultrasound images generated by the processor 130. For example, the display 140 may include at least one of a cathode-ray tube (CRT) display, a liquid crystal display (LCD), a plasma display panel (PDP), an organic light-emitting diode (OLED) display, a field emission display (FED), a light-emitting diode (LED) display, a vacuum fluorescent display (VFD), a digital light processing (DLP) display, a flat panel display (FPD), a three-dimensional (3D) display, and a transparent display, but is not limited thereto. According to an embodiment, the display 140 may be formed as a touch screen including a touch interface.

According to an embodiment, the display 140 may have a frame rate preset according to device characteristics and display the plurality of frames of ultrasound image by synchronizing them to the preset frame rate.

The ultrasound imaging apparatus 100 may further include a user input device (not shown). The user input device may receive a user's input information. According to an embodiment, the input information may include information about setting a region of interest (ROI) in a B mode image. The ROI may include a color box for obtaining a color Doppler mode image. In an embodiment, the user input device may include at least one of a control panel, a trackball, a mouse, and a keyboard.

FIG. 2 is a block diagram of a configuration of the ultrasound data acquisitor 110 according to an embodiment.

Referring to FIG. 2, the ultrasound data acquisitor 110 may include the ultrasound probe 210, the transmitter 220, the receiver 230, and the ultrasound data former 240.

The ultrasound probe 210 may include a plurality of transducers (212 of FIG. 3) that convert electrical signals into ultrasound signals or vice versa. The ultrasound probe 210 may produce receive signals by transmitting ultrasound signals to an object and receiving ultrasound echo signals reflected from the object. The receive signals may be analog signals. The ultrasound probe 210 may include a convex probe, a linear probe, and the like.

The transmitter 220 controls transmission of ultrasound signals. According to an embodiment, the transmitter 220 may produce first transmit signals for generating a B mode image. When the first transmit signals are provided from the transmitter 220, the ultrasound probe 210 may convert the first transmit signals into ultrasound signals and transmit the ultrasound signals to the object. The ultrasound probe 210 may then receive ultrasound echo signals reflected from the object to thereby produce first receive signals.

Furthermore, the transmitter 220 may produce second transmit signals for generating a color Doppler mode image showing an ROI based on an ensemble number. When the second transmit signals are provided from the transmitter 220, the ultrasound probe 210 may convert the second transmit signals into ultrasound signals and transmit the ultrasound signals to the object. The ultrasound probe 210 may then receive ultrasound echo signals reflected from the object to thereby produce second receive signals.

The receiver 230 produces digital signals by performing analog-to-digital conversion (ADC) on receive signals provided by the ultrasound probe 210. In an embodiment, the receiver 230 may produce a focused receive signal by performing receive focusing on the digital signals.

According to an embodiment, when the first receive signals are provided from the ultrasound probe 210, the receiver 230 may produce first digital signals by performing ADC on the first receive signals. The receiver 230 may then produce a first focused receive signal by performing receive focusing on the first digital signals. Furthermore, when the second receive signals are provided from the ultrasound probe 210, the receiver 230 may produce second digital signals by performing ADC on the second receive signals.

The receiver 230 may then produce a second focused receive signal by performing receive focusing on the second digital signals.

The ultrasound data former 240 form ultrasound data corresponding to an ultrasound image by using focused receive signals which are provided from the receiver 230. Furthermore, the ultrasound data former 240 may perform various signal processing operations (e.g., gain control, etc.), which are necessary for creating ultrasound data, on focused receive signals.

According to an embodiment, when the first focused receive signal is provided from the receiver 230, the ultrasound data former 240 may form first ultrasound data corresponding to a B mode image by using the first focused receive signal. The first ultrasound data may include RF data, but is not limited thereto. Furthermore, when the second focused receive signal is provided from the receiver 230, the ultrasound data former 240 may create second ultrasound data corresponding to a color Doppler mode image by using the second focused receive signal. The second ultrasound data may include IQ data, but is not limited thereto.

Figure 3:
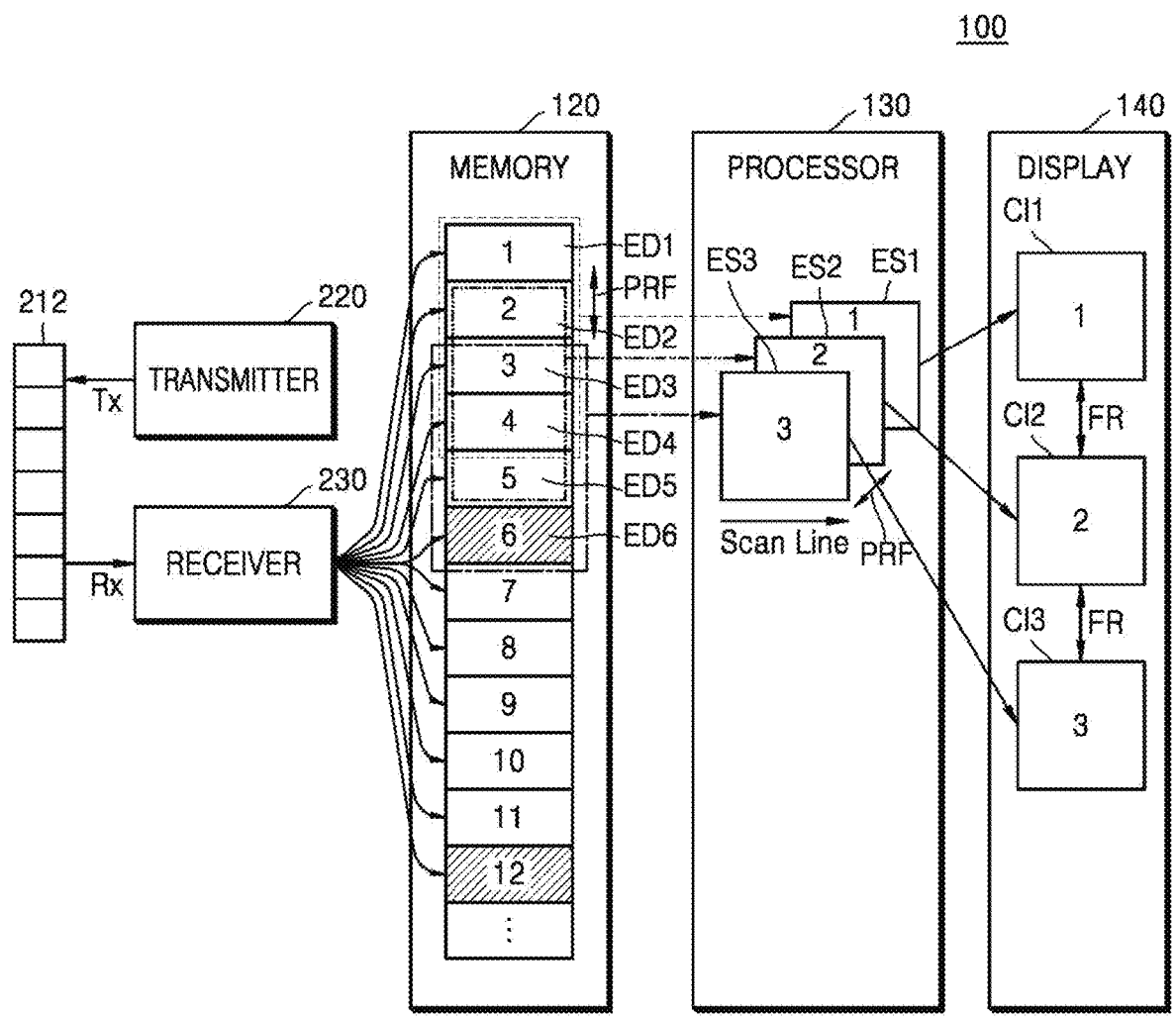
FIG. 3 is a diagram for explaining a method, performed by an ultrasound imaging apparatus, of generating a color Doppler mode image based on ultrasound data acquired from an object, according to an embodiment.

FIG. 3 is a diagram for explaining a method, performed by the ultrasound imaging apparatus 100, of generating a color Doppler mode image based on ultrasound data acquired from an object, according to an embodiment.

Referring to FIG. 3, the transmitter 220 may send transmit signals Tx for generating an ultrasound image of an object, and the receiver 230 may receive receive signals Rx from the transducers 212. According to an embodiment, the transmitter 220 may produce Doppler mode transmit signals corresponding to an ensemble number. The transmitter 220 may transmit the Doppler mode transmit signals via interleaved transmission (interleaved Tx). The receiver 230 may receive the receive signals Rx and perform beamforming on the receive signals Rx to thereby produce focused receive data. Since the transmitter 220 and the receiver 230 shown in FIG. 3 respectively correspond to the transmitter 220 and the receiver 230 described with reference to FIG. 2, detailed descriptions thereof will be omitted below.

The memory 120 may store a plurality of pieces of ensemble data acquired by the receiver 230. According to an embodiment, the plurality of pieces of ensemble data may be transmitted based on interleaved Tx and then acquired. As shown in FIG. 3, six (6) pieces of ensemble data may be stored in the memory 120 after one-time receiving of ultrasound signals. The six pieces of ensemble data including first through sixth ensemble data ED1 through ED6 may each be acquired at an interval of a PRF and then stored in the memory 120. Although FIG. 3 shows that ultrasound data produced after one-time receiving includes six pieces of ensemble data, this is for convenience only, and embodiments are not limited thereto.

The processor 130 may selectively extract four (4) pieces of ensemble data from among the six pieces of ensemble data. According to an embodiment, the processor 130 may generate a plurality of ensemble data sets by sequentially extracting four pieces of ensemble data in an overlapping manner while skipping extraction of one ensemble data from among the six pieces of ensemble data. In the embodiment shown in FIG. 3, the processor 130 may select and extract the first through fourth ensemble data ED1 through ED4 consecutively acquired and stored in the memory 120 and combine the extracted first through fourth ensemble data ED1 through ED4 into one group to thereby generate a first ensemble data set ES1. The processor 130 may also select and extract the second through fifth ensemble data ED2 through ED5 and combine the extracted second through fifth ensemble data ED2 through ED5 into a second ensemble data set ES2. Similarly, the processor 130 may select and extract the third through sixth ensemble data ED3 through ED6 and combine the extracted third through sixth ensemble data ED3 through ED6 into a third ensemble data set ES3. In this case, the first ensemble data ED1 and the sixth ensemble data ED6 may be selected and extracted only once, while the second through fifth ensemble data ED2 through ED5 may be selected and extracted at least twice. In other words, the processor 130 may select and extract at least once some ensemble data from among ultrasound data produced after one-time receive focusing. Although FIG. 3 shows that the processor 130 selectively extracts four pieces of ensemble data, this is for convenience only, and embodiments are not limited thereto.

The processor 130 may also generate a plurality of frames of first through third color Doppler mode images CI1 through CI3 by respectively using the first through third ensemble data sets ES1 through ES3. For example, the processor 130 may perform clutter filtering on the first through fourth ensemble data ED1 through ED4 in the first ensemble data set ES1 to remove a clutter signal and a noise signal and compute power and velocity components to generate the first color Doppler mode image CI1. In the same manner, the processor 130 may respectively generate the second and third color Doppler mode images CI2 and CI3 from the second and third ensemble data sets ES2 and ES3.

The display 140 may have a preset frame rate FR according to device characteristics. The processor 130 may arrange an interval at which frames in the first through third color Doppler mode images CI1 through CI3 are displayed to be equally spaced along a time axis, so that the interval is equal to in accordance with the preset frame rate FR for the display 140. The display 140 may display the first through third color Doppler mode images CI1 through CI3 at the preset frame rate FR.

In the embodiment shown in and described with reference to FIGS. 1 and 3, the ultrasound imaging apparatus 100 may selectively extract consecutively acquired ultrasound data corresponding to a processing ensemble number i from among N pieces of ensemble data produced after one-time receiving of ultrasound signals and generate a plurality of color Doppler mode images. Thus, according to the present embodiment, a color Doppler mode image may be generated at a high frame rate, compared to conventional imaging in which a single frame of color Doppler mode image is obtained with one-time receive focusing of ultrasound signals. This high frame rate imaging according to the embodiment may facilitate easy observation of movement of high velocity, high pressure blood flow such as arterial blood flow. Furthermore, according to the present embodiment, since it is possible to display motion of a fast moving object such as the heart wall as well as blood flow at a high frame rate for easier observation, this high frame rate imaging is also advantageous in a tissue Doppler image mode. However, according to the embodiment, since a single frame of color Doppler mode image is generated by selectively extracting only four pieces of ensemble data from among the six pieces of ensemble data ED1 through ED6, a signal to noise ratio (SNR) may be lowered to a certain extent, compared to conventional imaging.

Figure 4:
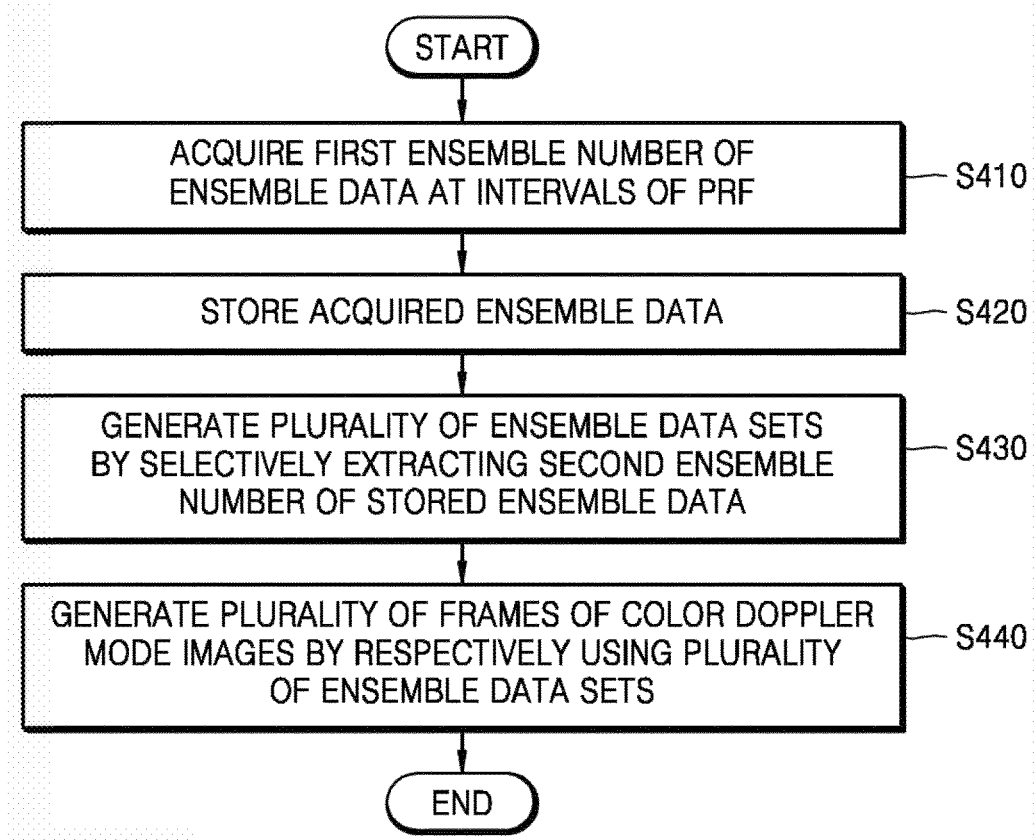
FIG. 4 is a flowchart of a method, performed by an ultrasound imaging apparatus, of generating a color Doppler mode image based on ultrasound data acquired from an object, according to an embodiment.

FIG. 4 is a flowchart of a method, performed by the ultrasound imaging apparatus 100, of generating a color Doppler mode image based on ultrasound data acquired from an object, according to an embodiment.

Referring to FIG. 4, the ultrasound imaging apparatus 100 acquires a first ensemble number of ensemble data at intervals of a PRF (S410). In an embodiment, the ultrasound imaging apparatus 100 may transmit ultrasound signals to the object at the PRF along a time axis and receive ultrasound echo signals reflected from the object. The ultrasound imaging apparatus 100 may transmit and receive the first ensemble number of ultrasound signals to and from the object in order to acquire Doppler signals corresponding to one scan line.

The ultrasound imaging apparatus 100 stores the acquired first ensemble number of ensemble data (S420). According to an embodiment, the ultrasound imaging apparatus 100 may store information necessary for distinguishing, among Doppler signals, blood flow signals resulting from the object, i.e., blood flow, clutter signals caused by movement of a vessel wall, and noise based on velocity and power components of the Doppler signals. According to an embodiment, the ultrasound imaging apparatus 100 may store RF data acquired based on ultrasound echo signals.

The ultrasound imaging apparatus 100 generates a plurality of ensemble data sets by selectively extracting a second ensemble number of the stored first ensemble number of ensemble data (S430). In an embodiment, the second ensemble number may be less than or equal to the first ensemble number. According to an embodiment, the ultrasound imaging apparatus 100 may sequentially extract the second ensemble number of ensemble data in an overlapping manner while skipping extraction of at least one ensemble data from among the ensemble data stored in operation S420. According to an embodiment, the ultrasound imaging apparatus 100 may extract each piece of the stored ensemble data at least once.

The ultrasound imaging apparatus 100 generates a plurality of frames of color Doppler mode images by respectively using the plurality of ensemble data sets (S440). In an embodiment, the ultrasound imaging apparatus 100 may acquire ultrasound data including RF data and IQ data by performing one-time receiving of ultrasound signals. The ultrasound imaging apparatus 100 may generate the plurality of frames of color Doppler mode images by using the plurality of ensemble data sets extracted from the IQ data while generating a B mode image based on the RF data. Thus, the ultrasound imaging apparatus 100 may generate a single frame of B mode image and the plurality of frames of color Doppler mode images by performing one-time receiving of ultrasound signals.

Figure 5:
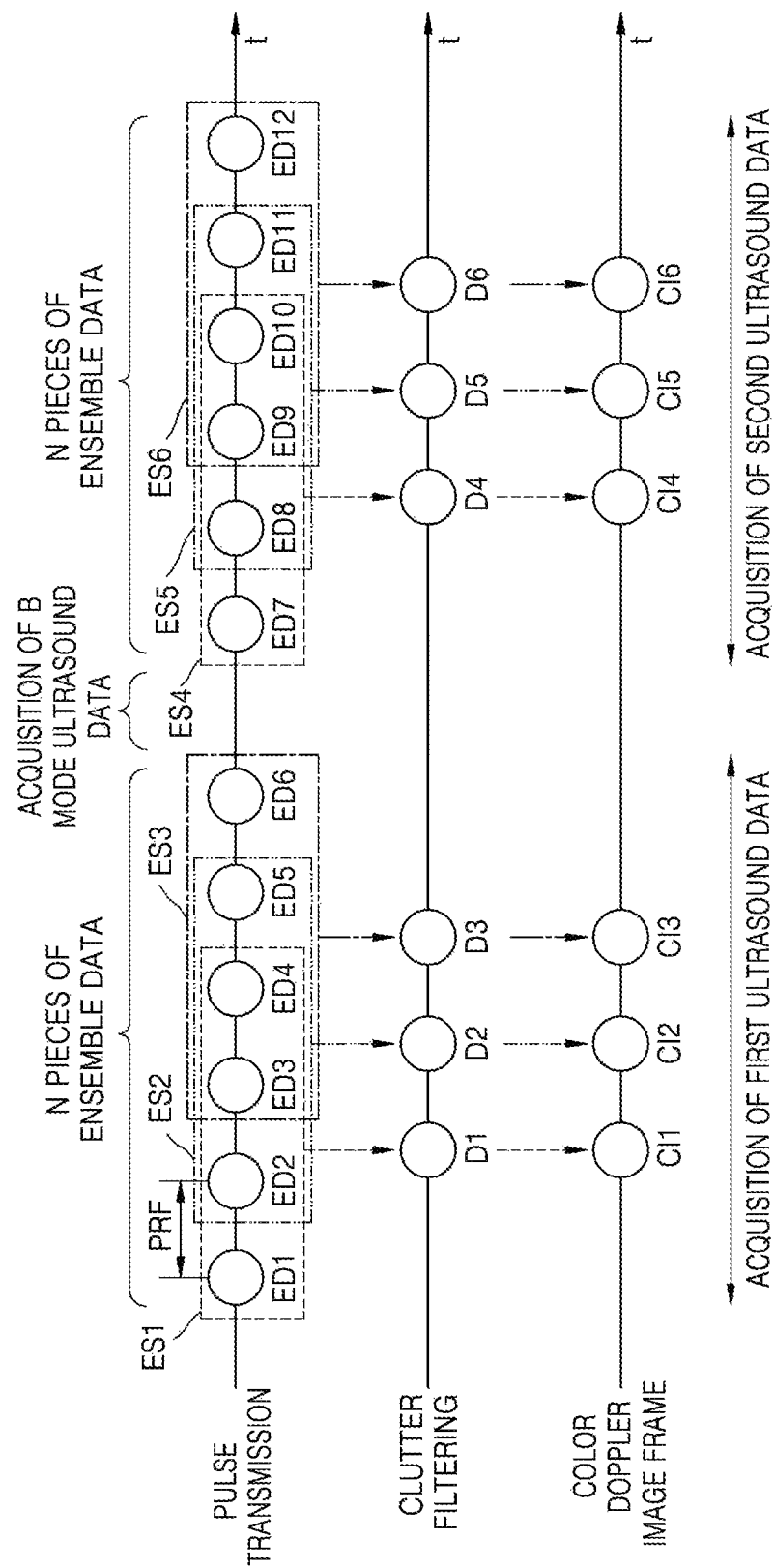
FIG. 5 is a diagram for explaining a method, performed by an ultrasound imaging apparatus, of generating color Doppler mode images based on a plurality of pieces of ensemble data, according to an embodiment.

FIG. 5 is a diagram for explaining a method, performed by the ultrasound imaging apparatus 100, of respectively generating color Doppler mode images CI1 through CI3 or CI4 through CI6 based on a plurality of pieces of ensemble data ED1 through ED6 or ED7 through ED12, according to an embodiment. For convenience, the plurality of pieces of ensemble data ED1 through ED6 or ED7 through ED12 are indicated as circles.

Referring to FIG. 5, the ultrasound imaging apparatus 100 may acquire N pieces of ensemble data ED1 through ED6 (ED7 through ED12) having an interval of a PRF along a time axis. In detail, the ultrasound imaging apparatus 100 may acquire the N pieces of ensemble data ED1 through ED6 from first ultrasound data that are transmitted via interleaving and acquired and then acquire next N pieces of ensemble data ED7 through ED12 from second ultrasound data. According to an embodiment, the ultrasound imaging apparatus 100 may acquire B mode ultrasound data between acquisitions of the first and second ultrasound data. In an embodiment, the B mode ultrasound data may be RF data.

In the embodiment shown in FIG. 5, N denotes the number of pieces of ensemble data in ultrasound data produced by one-time receiving, and may be six (6). However, this is for convenience only, and embodiments are not limited thereto. The ultrasound imaging apparatus 100 may acquire first through sixth ensemble data ED1 through ED6 via acquisition of the first ultrasound data. The ultrasound imaging apparatus 100 may also acquire seventh through twelfth ensemble data ED7 through ED12 via acquisition of the second ultrasound data. According to an embodiment, the ultrasound imaging apparatus 100 may combine the first through sixth ensemble data ED1 through ED6 and the B mode ultrasound data into one group for storage. The ultrasound imaging apparatus 100 may also combine the seventh through twelfth ensemble data ED7 through ED12 and B mode ultrasound data into one group for storage.

The ultrasound imaging apparatus 100 may selectively extract, from among the first through sixth ensemble data ED1 through ED6, a total of four (4) pieces of ensemble data including the first through fourth ensemble data ED1 through ED4 consecutively acquired along the time axis. In other words, the ultrasound imaging apparatus 100 may sequentially extract four pieces of ensemble data in an overlapping manner while skipping extraction of at least one ensemble data from among six pieces of ensemble data. The ultrasound imaging apparatus 100 may combine the extracted first through fourth ensemble data ED1 through ED4 into a first ensemble data set ES1. Similarly, the ultrasound imaging apparatus 100 may selectively extract the second through fifth ensemble data ED2 through ED5 and combine them into a second ensemble data set ES2, and extract the third through sixth ensemble data ED3 through ED6 and combine them into a third ensemble data set ES3.

The ultrasound imaging apparatus 100 may perform clutter filtering to remove clutter signals and noise signals respectively included in the first through third ensemble data sets ES1 through ES3. After undergoing the clutter filtering, the first through third ensemble data sets ES1 through ES3 may be used to form first through third Doppler data D1 through D3, respectively.

According to an embodiment, the ultrasound imaging apparatus 100 may remove a clutter signal and a noise signal from the first ensemble data set ES1 to thereby generate the first Doppler data D1. In the same manner, the ultrasound imaging apparatus 100 may remove clutter signals and noise signals respectively from the first and second ensemble data sets ES2 and ES3 to thereby generate the second Doppler data D2 and the third Doppler data D3.

A clutter filter may be a filter used to remove clutter signals that are low frequency Doppler signals within ensemble data included in the first through third ensemble data sets ES1 through ES3. According to an embodiment, the clutter filter may be a high pass filter (HPF), and may be implemented as a matrix infinite impulse response (IIR) filter. However, embodiments are not limited thereto, and the clutter filter may be implemented as a finite impulse response (FIR) filter.

The ultrasound imaging apparatus 100 may calculate power components and velocity components contained in the first through third Doppler data D1 through D3 to generate a plurality of frames of color Doppler mode images CI1 through CI3. Furthermore, the ultrasound imaging apparatus 100 may generate a B mode image based on acquired RF data.

In the embodiment shown in FIG. 5, the ultrasound imaging apparatus 100 may acquire N (i.e., six) pieces of ensemble data ED1 through ED6 and B mode ultrasound data via one-time receiving of ultrasound signals and generate a plurality of frames of color Doppler mode images CI1 through CI6 based on the N pieces of ensemble data ED1 through ED6. According to the present embodiment, it is possible to increase a frame rate at which a color Doppler mode image is displayed, thereby facilitating observation of fast motion of an object such as blood flow or the heart wall.

Figure 6:
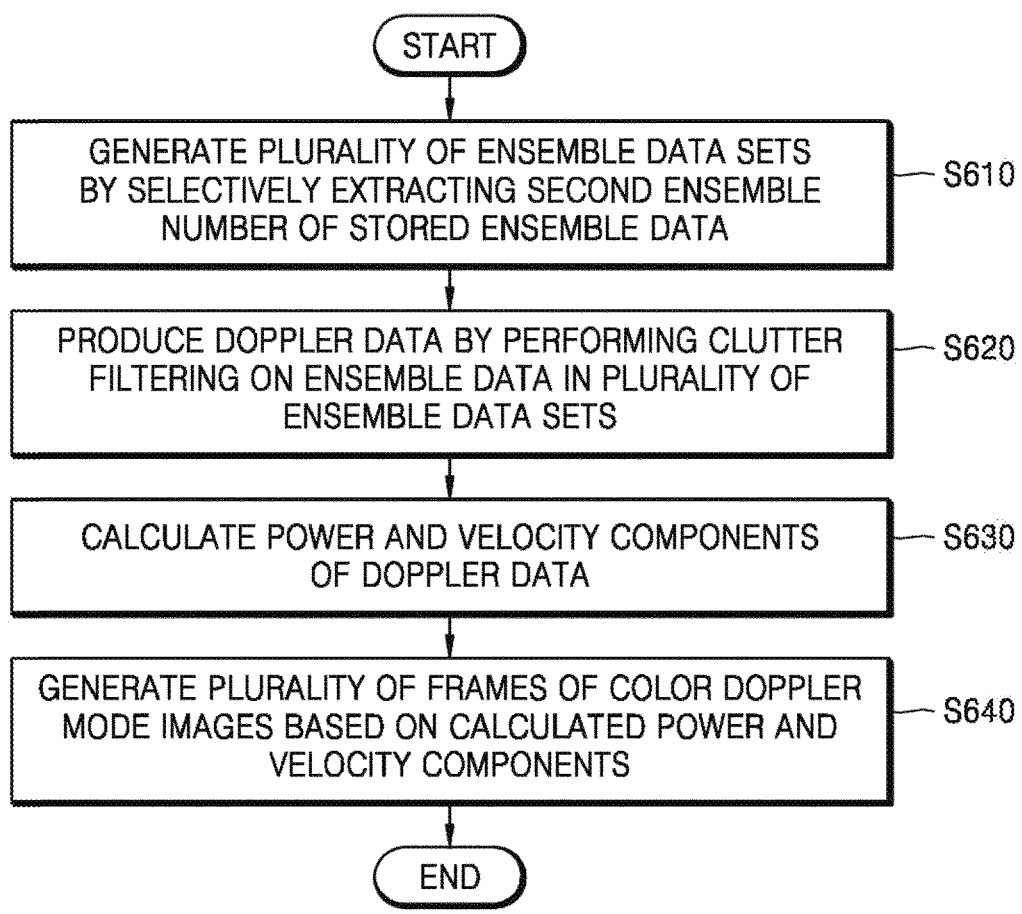
FIG. 6 is a flowchart of a method, performed by an ultrasound imaging apparatus, of generating color Doppler mode images based on a plurality of pieces of ensemble data, according to an embodiment.

FIG. 6 is a flowchart of a method, performed by the ultrasound imaging apparatus 100, of generating color Doppler mode images based on a plurality of pieces of ensemble data, according to an embodiment.

Referring to FIG. 6, the ultrasound imaging apparatus 100 generates a plurality of ensemble data sets by selectively extracting a second ensemble number of ensemble data stored in the memory (120 of FIGS. 1 and 3) (S610). According to an embodiment, the memory 120 may store a first ensemble number of ensemble data and RF data. The ensemble data may include blood flow signals resulting from an object, e.g., blood flow, clutter signals caused by movement of a vessel wall, etc., and noise. In an embodiment, the second ensemble number may be less than or equal to the first ensemble number. The ultrasound imaging apparatus 100 may sequentially extract the second ensemble number of ensemble data in an overlapping manner while skipping extraction of at least one ensemble data from among the first ensemble number of ensemble data.

The ultrasound imaging apparatus 100 produces Doppler data by performing clutter filtering on the ensemble data in the plurality of ensemble data sets (S620). The ultrasound imaging apparatus 100 may perform clutter filtering to remove clutter signals and noise signals in the plurality of ensemble data sets. The clutter filter may be a HPF. For example, the clutter filter may be implemented as a matrix IRR filter or FIR filter.

The ultrasound imaging apparatus calculates power components and velocity components of the Doppler data (S630). According to an embodiment, the ultrasound imaging apparatus 100 may compute power values by adding the real part I and a square of the imaginary part Q of the ensemble data in the plurality of ensemble data sets and obtain velocity components by calculating an average velocity of each ensemble data. However, embodiments are not limited thereto, and the power and velocity components of the Doppler data may be calculated using various methods known in the art.

The ultrasound imaging apparatus 100 generates a plurality of frames of color Doppler mode images based on the calculated power components and velocity components (S640). According to an embodiment, the ultrasound imaging apparatus 100 may acquire B mode ultrasound data by performing processing such as amplification, logarithmic compression, and envelope detection on ultrasound echo signals reflected from the object. In this case, the ultrasound imaging apparatus 100 may generate a B mode image based on the acquired B mode ultrasound data.

In the embodiment shown in FIGS. 5 and 6, the ultrasound imaging apparatus 100 may generate a plurality of frames of color Doppler mode images and a single frame of B mode image based on a focused receive signal produced by one-time receiving of ultrasound signals.

Figure 7:
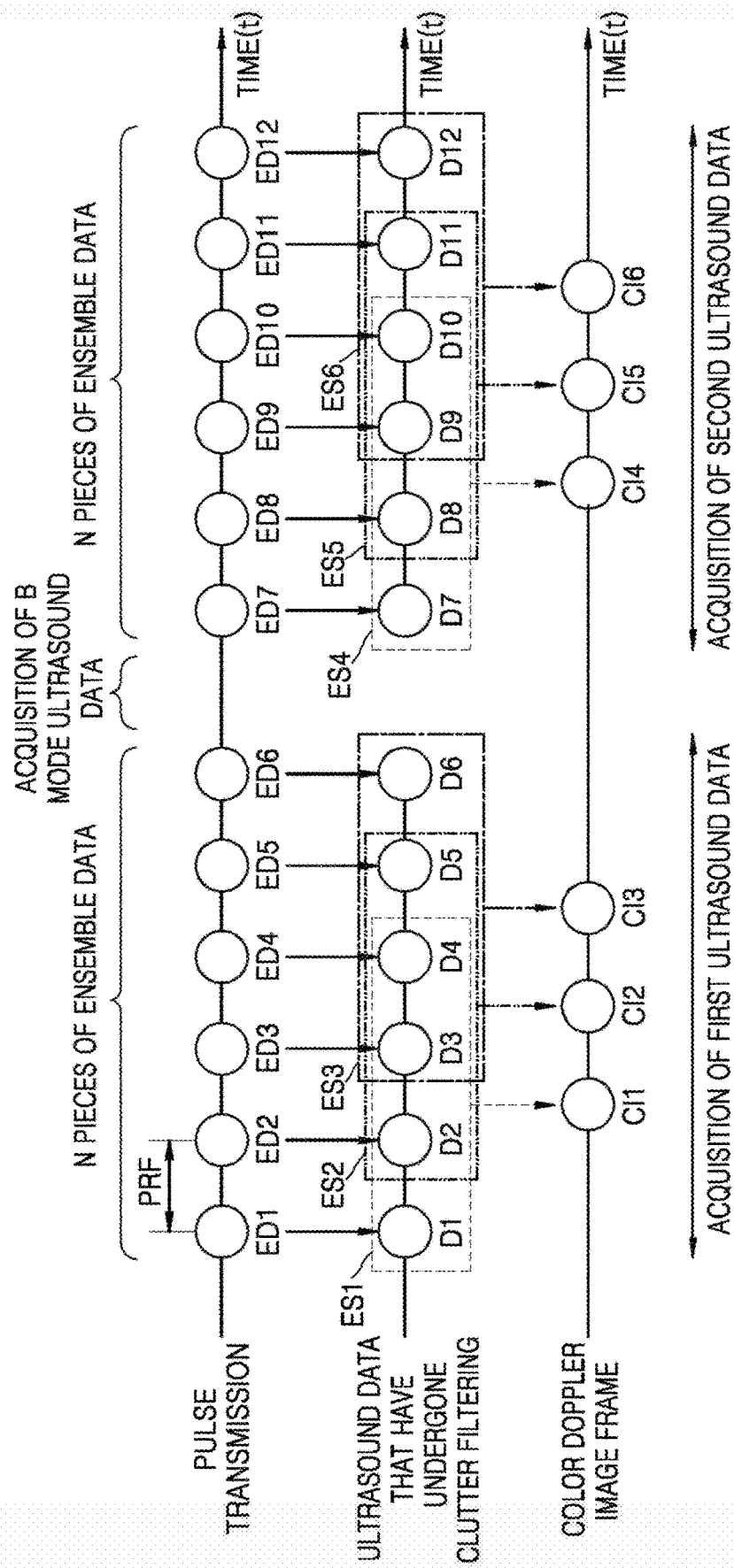
FIG. 7 is a diagram for explaining a method, performed by an ultrasound imaging apparatus, of generating color Doppler mode images based on a plurality of pieces of ensemble data, according to an embodiment.

FIG. 7 is a diagram for explaining a method, performed by the ultrasound imaging apparatus 100, of generating color Doppler mode images CI1 through CI3 or CI4 through CI6 based on a plurality of pieces of ensemble data ED1 through ED6 or ED7 through ED12, according to an embodiment.

Referring to FIG. 7, the ultrasound imaging apparatus 100 may acquire N pieces of ensemble data ED1 through ED6

(ED7 through ED12) having an interval of a PRF along a time axis. In detail, the ultrasound imaging apparatus 100 may acquire the N pieces of ensemble data ED1 through ED6 from first ultrasound data transmitted via interleaving and produced by receiving and then acquire next N pieces of ensemble data ED7 through ED12 from second ultrasound data produced by receiving. According to an embodiment, the ultrasound imaging apparatus 100 may acquire B mode ultrasound data between receptions of the first and second ultrasound data.

The ultrasound imaging apparatus 100 may produce a plurality of pieces of Doppler data, i.e. N pieces of Doppler data D1 through D6 or D7 through D12, by respectively performing clutter filtering on the N pieces of ensemble data ED1 through ED6 or ED7 through ED12. The ultrasound imaging apparatus 100 may perform the clutter filtering to remove clutter signals and noise signals respectively included in the plurality of pieces of ensemble data ED1 through ED6 and ED7 through ED12. In an embodiment, a clutter filter may be HPF, and may be implemented as a matrix type IIR filter.

After performing the clutter filtering, the ultrasound imaging apparatus 100 may store the N pieces of Doppler data D1 through D6 in the memory 120. The N pieces of Doppler data D1 through D6 stored in the memory 120 may include IQ data.

According to an embodiment, the ultrasound imaging apparatus 100 may selectively extract, from among the N pieces of Doppler data D1 through D6, a total of four (4) pieces of Doppler data including first through fourth Doppler data D1 through D4 consecutively acquired along a time axis. The ultrasound imaging apparatus 100 may combine the extracted first through fourth Doppler data D1 through D4 into a first ensemble data set ES1. Similarly, the ultrasound imaging apparatus 100 may selectively extract second through fifth Doppler data D2 through D5 and combine them into a second ensemble data set ES2. The ultrasound imaging apparatus 100 may also selectively extract third through sixth Doppler data D3 through D6 and combine them into a third ensemble data set ES3.

Thereafter, the ultrasound imaging apparatus 100 may generate a plurality of frames of color Doppler mode images CI1 through CI3 by using the first through third ensemble data sets ES1 through ES3.

Figure 8:
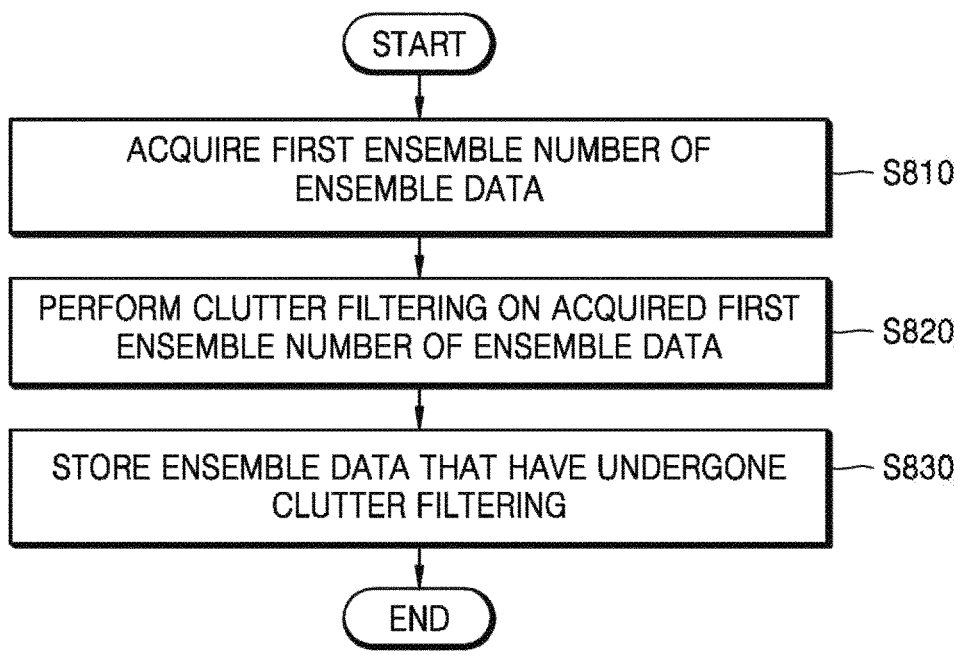
FIG. 8 is a flowchart of a method, performed by an ultrasound imaging apparatus, of performing clutter filtering on acquired ensemble data, according to an embodiment.

FIG. 8 is a flowchart of a method, performed by the ultrasound imaging apparatus 100, of performing clutter filtering on acquired ensemble data, according to an embodiment.

The ultrasound imaging apparatus acquires a first ensemble number of ensemble data at intervals of a PRF (S810). Since operation S810 corresponds to operation S410 described with reference to FIG. 4, a detailed description thereof will be omitted here.

The ultrasound imaging apparatus 100 performs clutter filtering on the acquired first ensemble number of ensemble data (S820). The ultrasound imaging apparatus 100 may form a plurality of pieces of Doppler data by performing the clutter filtering to remove clutter signals and noise signals in the ensemble data.

The ultrasound imaging apparatus 100 stores the ensemble data that have undergone the clutter filtering (S830). According to an embodiment, the ensemble data that have undergone the clutter filtering may include IQ data. The embodiment shown in FIGS. 7 and 8 is different from the embodiment shown in FIG. 5 in that the ultrasound imaging apparatus 100 produces Doppler data by performing clutter filtering before selectively extracting ensemble data, which are acquired based on ultrasound echo signals reflected from the object, and removing clutter signals and noise signals in the ensemble data and then selectively extract the Doppler data. Thus, descriptions of the ultrasound imaging apparatus 100 already provided above with reference to FIG. 5 will be omitted below, and only the difference in the order of operations, i.e., clutter filtering and selective extraction of ensemble data, will be described.

Figure 9:
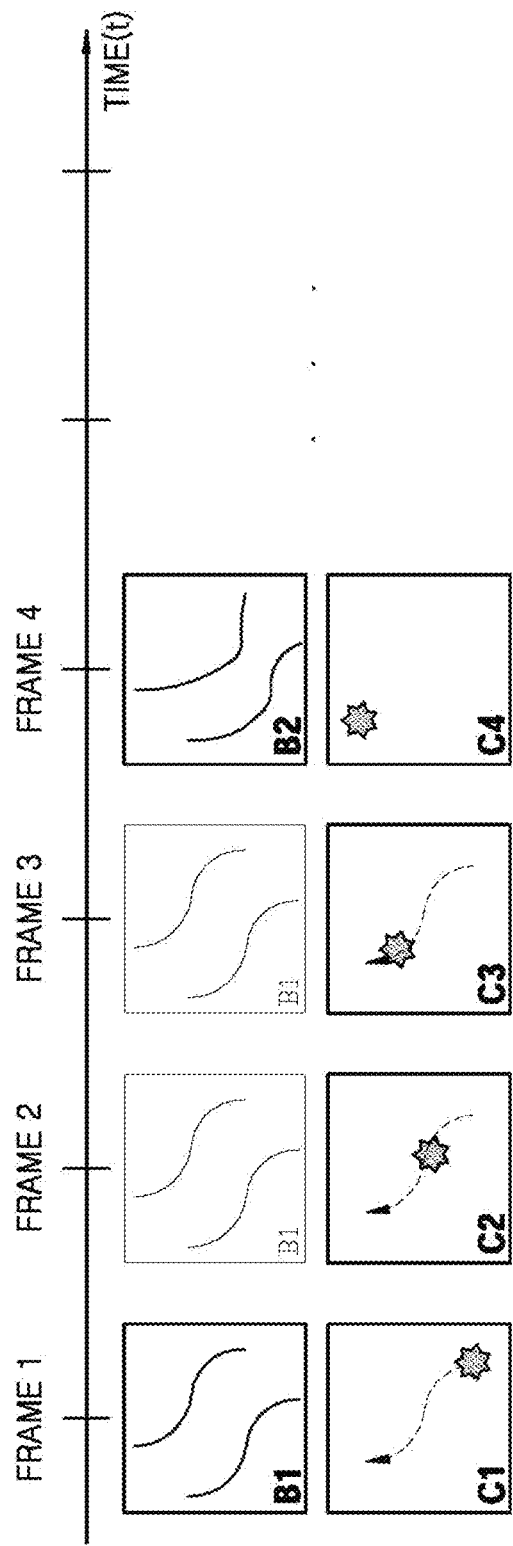
FIG. 9 is a diagram for explaining a method, performed by an ultrasound imaging apparatus, of generating brightness (B) mode images and color Doppler mode images based on ultrasound data acquired from an object, according to an embodiment.

FIG. 9 is a diagram for explaining a method, performed by the ultrasound imaging apparatus 100, of generating B mode images B1 and B2 and color Doppler mode images C1 through C4 based on ultrasound data acquired from an object, according to an embodiment.

Referring to FIG. 9, the ultrasound imaging apparatus 100 may acquire ultrasound data based on ultrasound echo signals reflected from the object and generate the B mode images B1 and B2 and the color Doppler mode images C1 through C4 based on the acquired ultrasound data. According to an embodiment, the ultrasound imaging apparatus 100 may generate a single frame of B mode image B1, i.e., a first B mode image B1, and a plurality of color Doppler mode images C1 through C3, i.e., first through third color Doppler mode images C1 through C3, based on acquired first ultrasound data. In detail, like in the embodiments shown in and described with reference to FIGS. 5 through 8, the ultrasound imaging apparatus 100 may obtain the first B mode image B1 based on RF data included in ultrasound data acquired at one time and generate three frames of color Doppler mode images including the first through third color Doppler mode images C1 through C3 by selectively extracting consecutive acquired ensemble data from among a plurality of pieces of ensemble data included in the ultrasound data.

In the embodiment shown in FIG. 9, the three frames of first through third color Doppler mode images C1 through C3 are generated and displayed with respect to a single frame of a B mode image B1. This method may provide improved interconnectivity among the first through third color Doppler mode images C1 through C3 compared to a conventional method whereby a single frame of color Doppler mode image is combined and displayed together with a single frame of B mode image. Furthermore, the ultrasound imaging apparatus 100 may provide interim images (the second and third color Doppler mode images C2 and C3 of FIG. 9) having high reliability compared to when using conventional frame interpolation, thereby allowing a user to easily observe a motion of blood flow in arteries or a motion of the heart wall.

Figure 10:
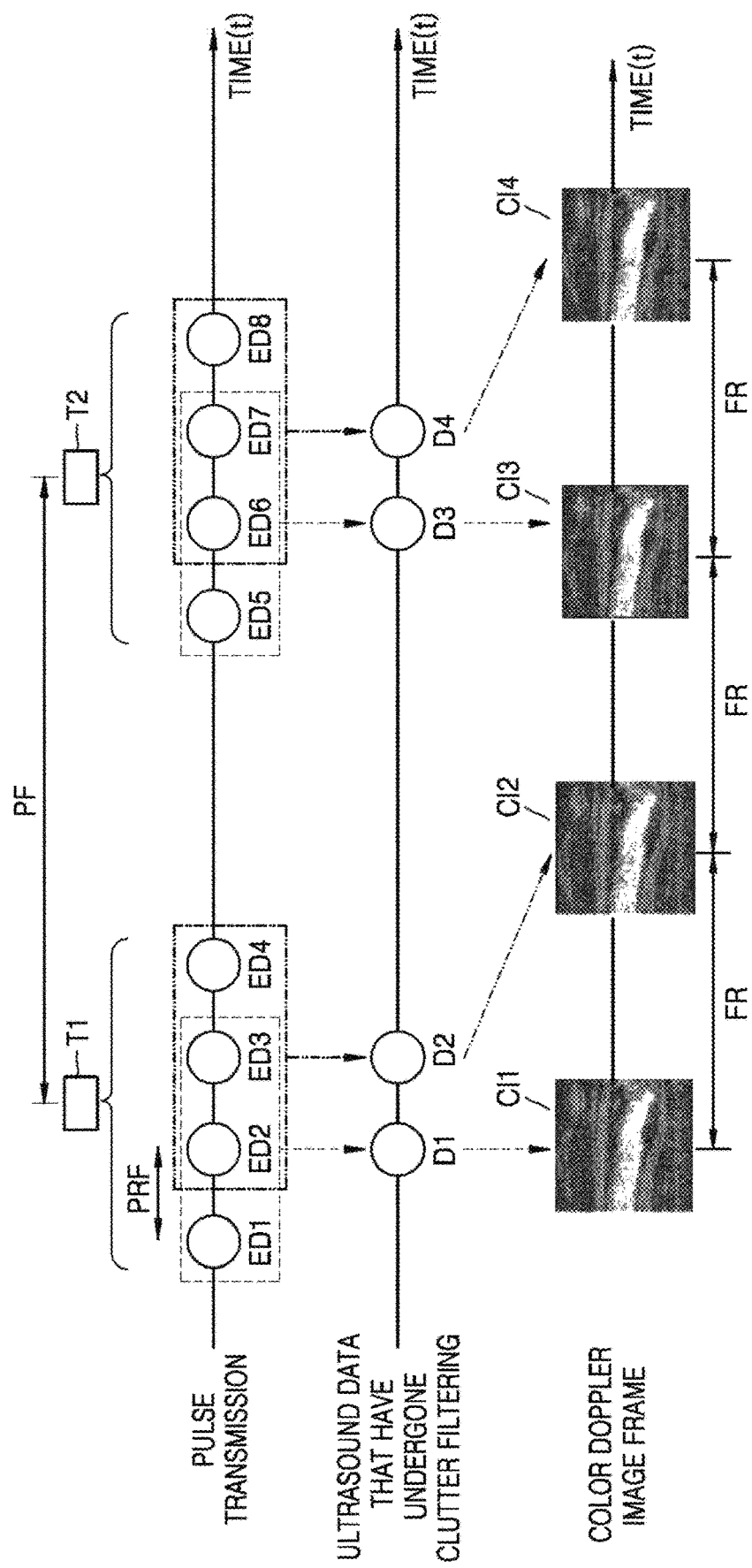
FIG. 10 is a diagram for explaining a method, performed by an ultrasound imaging apparatus, of displaying color Doppler mode images generated based on a plurality of pieces of ensemble data, according to an embodiment.

FIG. 10 is a diagram for explaining a method, performed by the ultrasound imaging apparatus 100, of displaying color Doppler mode images generated based on a plurality of pieces of ensemble data ED1 through ED8, according to an embodiment.

Referring to FIG. 10, the ultrasound imaging apparatus 100 may transmit ultrasound signals to an object and acquire first ultrasound data T1 and second ultrasound data T2 based on ultrasound echo signals reflected from the object. The ultrasound imaging apparatus 100 may acquire the first ultrasound data T1 and the second ultrasound data T2 at intervals of a pulse frequency (PF). The ultrasound imaging apparatus 100 may selectively extract consecutively acquired three pieces of ensemble data from among first through fourth ensemble data ED1 through ED4. For example, the ultrasound imaging apparatus 100 may select and extract the first through third ensemble data ED1 through ED3 or the second through fourth ensemble data ED2 through ED4 at one time. Similarly, the ultrasound imaging apparatus 100 may acquire fifth through eighth ensemble data ED5 through ED8 from the second ultrasound data T2 and selectively extract consecutively acquired three pieces of ensemble data from among the fifth through eighth ensemble data ED5 through ED8.

The ultrasound imaging apparatus 100 respectively combines the extracted three pieces of ensemble data into a plurality of ensemble data sets and produces a plurality of pieces of Doppler data D1 and D2 by removing clutter signals and noise signals included in the plurality of ensemble data sets via clutter filtering. Thereafter, the ultrasound imaging apparatus 100 may calculate power and velocity components of the plurality of pieces of Doppler data D1 and D2 to generate a plurality of frames of first through fourth color Doppler mode images CI1 through CI4.

According to an embodiment, the ultrasound imaging apparatus 100 may arrange the generated plurality of frames of first through fourth color Doppler mode images CI1 through CI4 at equally spaced intervals along a time axis, so that each interval is equal to a frame rate at which each of the plurality of frames of first through fourth color Doppler mode images CI1 through CI4 is displayed on the display (140 of FIG. 1). The display 140 of the ultrasound imaging apparatus 100 has a preset frame rate. For example, if the preset frame rate is 60 Hz, the ultrasound imaging apparatus 100 may arrange the first and second color Doppler mode images CI1 and CI2 by setting an interval on the time axis between the first and second color Doppler mode images CI1 and CI2 to 60 Hz. In the same way, the ultrasound imaging apparatus may respectively set intervals between the second and third color Doppler mode images CI2 and CI3 and between the third and fourth color Doppler mode images CI3 and CI4 to 60 Hz for arrangement. In other words, the ultrasound imaging apparatus 100 may set a frame rate FR of the plurality of frames of first through fourth color Doppler mode images CI1 through CI4 to be equal to a frame rate for the display 140 and display the plurality of frames of first through fourth color Doppler mode images CI1 through CI4 on the display 140 at the set frame rate FR.

In the embodiment shown in FIG. 10, since two frames of color Doppler mode images are generated respectively from the first ultrasound data T1 and the second ultrasound data T2, the frame rate FR of the first through fourth color Doppler mode images CI1 through CI4 may be double the PF. If the PF is 10 Hz, the frame rate FR of the first through fourth color Doppler mode images CI1 through CI4 may be set to 20 Hz. If the PF is 30 Hz, the frame rate FR thereof may be set to 60 Hz.

In general, since a PRF is significantly greater than a PF, if a plurality of frames of color Doppler mode images are generated based on ultrasound data acquired via one-time receiving, the plurality of frames of color Doppler mode images may be displayed for a short time. According to the embodiment shown in FIG. 10, the ultrasound imaging apparatus 100 may display the plurality of frames of first through fourth color Doppler mode images CI1 through CI4 generated at intervals of a PRF at the same frame rate FR as the preset frame rate for the display 140, thereby allowing a user to easily observe a fast motion of blood flow or the heart wall.

Figure 11:
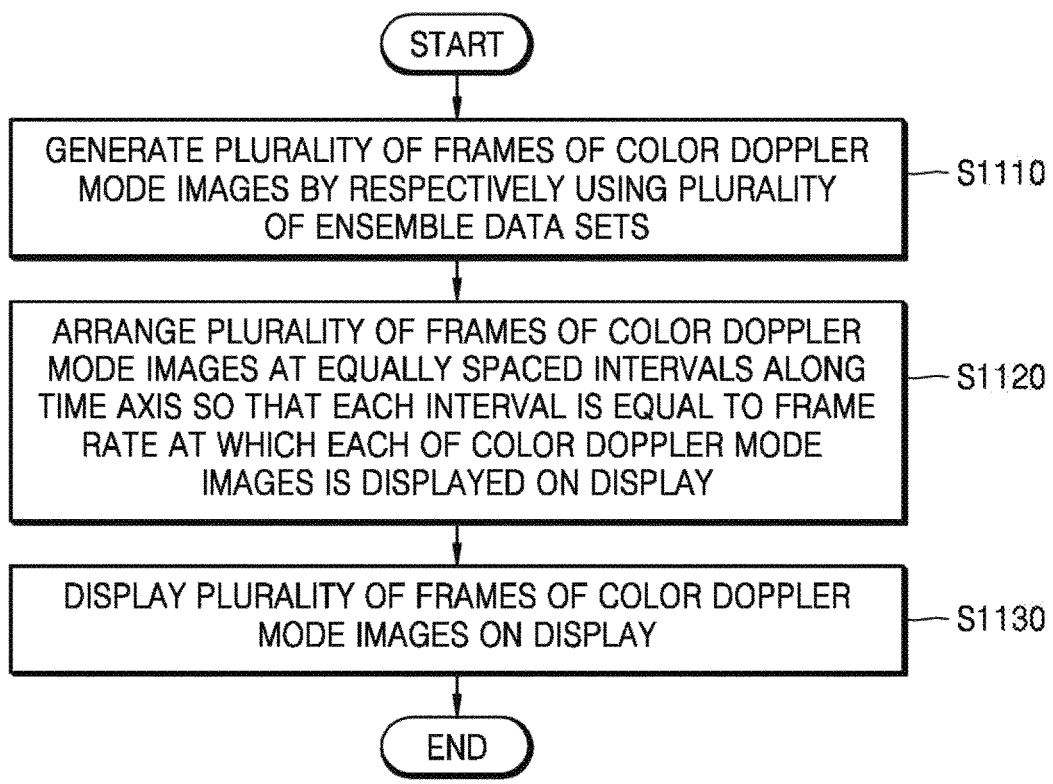
FIG. 11 is a flowchart of a method, performed by an ultrasound imaging apparatus, of displaying color Doppler mode images generated based on a plurality of pieces of ensemble data, according to an embodiment.

FIG. 11 is a flowchart of a method, performed by the ultrasound imaging apparatus 100, of displaying color Doppler mode images generated based on a plurality of pieces of ensemble data, according to an embodiment The ultrasound imaging apparatus 100 generates a plurality of frames of color Doppler mode images by respectively using a plurality of ensemble data sets (S1110). In an embodiment, the ultrasound imaging apparatus 100 may selectively extract consecutively acquired ensemble data from among a plurality of pieces of ensemble data and combine the extracted ensemble data respectively into a plurality of ensemble data sets. Furthermore, the ultrasound imaging apparatus 100 may perform clutter filtering on the plurality of ensemble data sets and compute power and velocity components to generate the plurality of frames of color Doppler mode images. Descriptions thereof are already provided above with reference to operations S410 through S440, and thus will not be repeated below.

The ultrasound imaging apparatus 100 arranges the plurality of frames of color Doppler mode images at equally spaced intervals along a time axis so that each interval is equal to a frame rate at which each of the plurality of frames of color Doppler mode images is displayed on the display 140 (S1120). The display 140 of the ultrasound imaging apparatus 100 has a frame rate preset according to a type and characteristics of the display 140, and the ultrasound imaging apparatus 100 may set an interval on the time axis between adjacent ones of the plurality of color Doppler mode images to be equal to the preset frame rate for the display 140.

The ultrasound imaging apparatus 100 displays the plurality of frames of color Doppler mode images on the display 140 (S1130).

Figure 12:
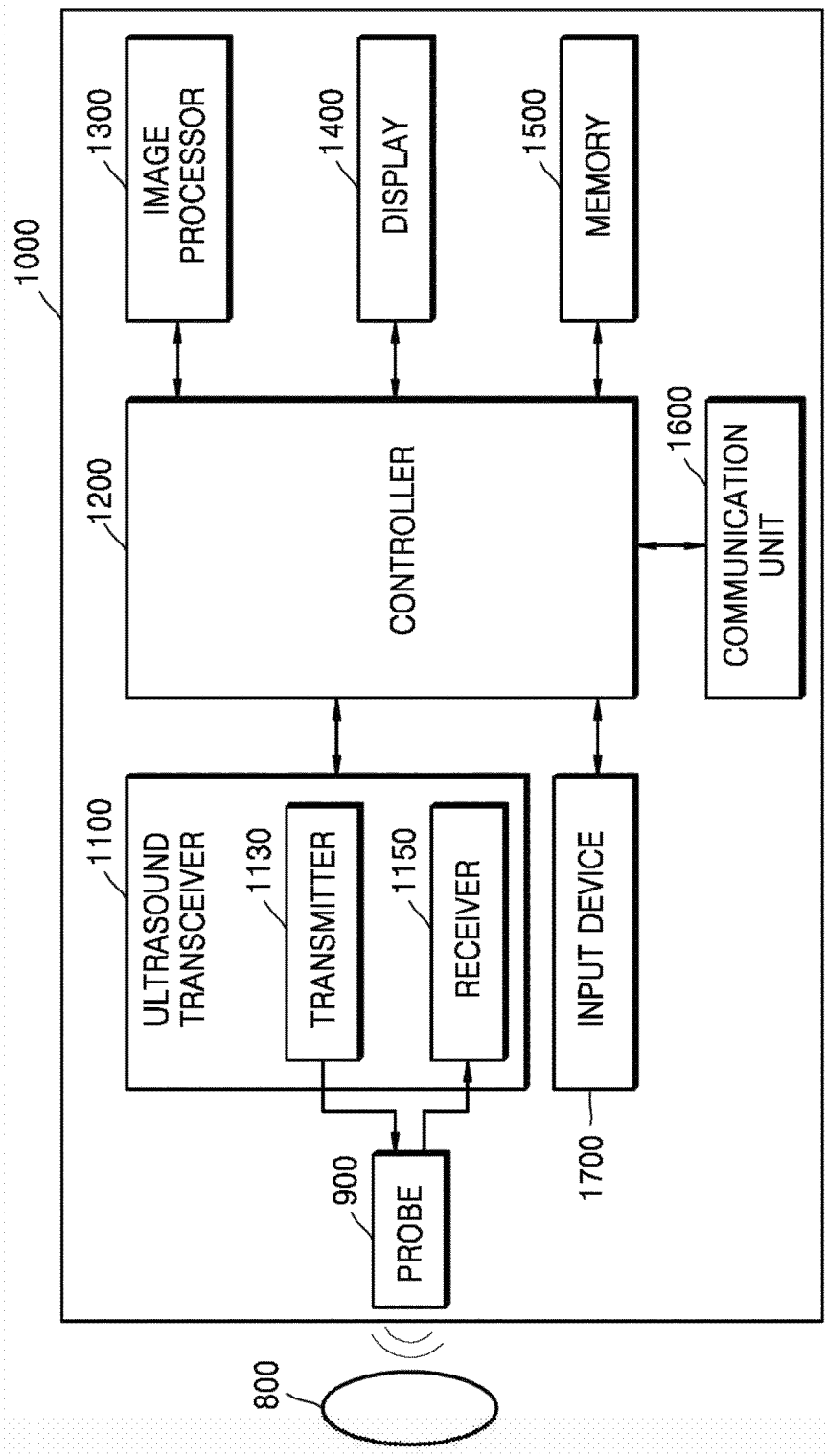
FIG. 12 is a block diagram of a configuration of an ultrasound imaging apparatus according to an embodiment.

FIG. 12 is a block diagram of a configuration of an ultrasound imaging apparatus 1000 according to an embodiment. The ultrasound imaging apparatus 1000 according to the present embodiment may include a probe 900, an ultrasound transceiver 1100, a controller 1200, an image processor 1300, a display 1400, a memory 1500, a communication unit 1600, and an input device 1700.

The ultrasound imaging apparatus 1000 may be a cart type apparatus or a portable type apparatus. Examples of portable ultrasound imaging apparatuses may include, but are not limited to, a smart phone including a probe and an application, a laptop computer, a PDA, and a tablet PC.

The probe 900 may include a plurality of transducers. The plurality of transducers transmit ultrasound signals to an object 800 based on a transmit signal applied by a transmitter 1130. The plurality of transducers may also receive ultrasound signals reflected from the object 800 to produce receive signals. Furthermore, the probe 900 may be integrally formed with the ultrasound imaging apparatus 1000 or be separate from the ultrasound imaging apparatus 1000 while being connected thereto by wire or wirelessly. In addition, the ultrasound imaging apparatus 1000 may include one or more probes 900 according to its implemented configuration.

The controller 1200 controls the transmitter 1130 to produce transmit signals to be applied respectively to the plurality of transducers in consideration of locations of the transducers 900 in the probe 900 and focal points.

The controller 1200 may perform ADC on the receive signals received from the probe 900 and control a receiver 1150 to create ultrasound data by summing digital receive signals in consideration of the locations of the plurality of transducers and focal points.

The image processor 1300 generates an ultrasound image based on the ultrasound data created by the receiver 1150.

The display 1400 may display the generated ultrasound image and various pieces of information processed by the ultrasound imaging apparatus 1000. The ultrasound imaging apparatus 1000 may include one or more displays 1400 according to its implemented configuration. Furthermore, the display 1400 may be combined with a touch panel to form a touch screen.

The controller 1200 may control overall operations of the ultrasound imaging apparatus 1000 and flow of signals among components within the ultrasound imaging apparatus 1000. The controller 1200 may further include a memory configured to store programs or data for performing functions of the ultrasound imaging apparatus 1000 and a processor configured to process the programs or data. Furthermore, the controller 1200 may receive a control signal from the input device 1700 or an external device to control operations of the ultrasound imaging apparatus 1000.

The ultrasound imaging apparatus 1000 may include the communication unit 1600 and be connected to externals device such as a server, a medical apparatus, a portable device (e.g., a smart phone, a tablet PC, or a wearable device), etc.

The communication unit 1600 may include at least one component that enables communication with an external device. For example, the communication unit 1600 may include at least one of a local area communication module, a wired communication module, and a wireless communication module.

The communication unit 1600 may receive a control signal and data from an external device and transmit the received control signal to the controller 1200 so that the controller 1200 may control the ultrasound imaging apparatus 1000 according to the received control signal.

Alternatively, by transmitting a control signal to an external device via the communication unit 1600, the controller 1200 may control the external device according to the control signal.

For example, the external device may process data according to a control signal received from the controller 1200 via the communication unit 1600.

A program for controlling the ultrasound imaging apparatus 1000 may be installed on the external device and may include instructions for performing some or all of the operations of the controller 1200.

The program may be preinstalled on the external device, or a user of the external device may download the program from a server providing an application for installation. The server providing an application may include a recording medium having the program recorded thereon.

The memory 1500 may store various data or programs for driving and controlling the ultrasound imaging apparatus 1000, input/output ultrasound data, obtained ultrasound images, etc.

The input device 1700 may receive user inputs for controlling the ultrasound imaging apparatus 1000. For example, the user inputs may include, but are not limited to, inputs for manipulating a button, a keypad, a mouse, a trackball, a jog switch, a knob, etc. an input for touching a touch pad or touch screen, a voice input, a motion input, an input of biometric information (e.g., iris recognition, fingerprint recognition, etc.), etc.

Examples of the ultrasound imaging apparatus 1000 will now be described in detail with reference to FIGS. 13A through 13C.

FIGS. 13A through 13C illustrate ultrasound imaging apparatuses 1000a through 1000c according to embodiments.

Referring to FIGS. 13A and 13B, the ultrasound imaging apparatuses 1000a and 1000b may each include a main display 1210 and a sub display 1220. One of the main display 1210 and the sub display 1220 may be formed as a touch screen. The main display 1210 and the sub display 1220 may display ultrasound images or various pieces of information processed by the ultrasound imaging apparatus 1000a or 1000b. Furthermore, the main display 1210 or the sub display 1220 may be formed as a touch screen and provide a graphical user interface (GUI) that receives data for controlling the ultrasound imaging apparatus 1000a or 1000b from a user. For example, the main display 1210 may display an ultrasound image, and the sub display 1220 may display a control panel for controlling display of the ultrasound image in the form of a GUI. The sub display 1220 may receive data for controlling display of an image via the control panel provided in the form of a GUI. The ultrasound imaging apparatus 1000a or 1000b may control display of the ultrasound image on the main display 1210 based on the received control data.

Referring to FIG. 13B, unlike the ultrasound imaging apparatus 1000a, the ultrasound imaging apparatus 1000b may further include a control panel 1650. The control panel 1650 may include buttons, a trackball, a jog switch, a knob, etc., and receive data for controlling the ultrasound imaging apparatus 1000b from the user. For example, the control panel 1650 may include a time gain compensation (TGC) button 1710, a Freeze button 1720, etc. The TGC button 1710 is used to set TGC values according to depths in an ultrasound image. Furthermore, when an input of the Freeze button 1720 is detected at a corresponding time point during capturing of an ultrasound image, the ultrasound imaging apparatus 1000b may maintain a state in which a frame image corresponding to the time point is displayed.

In addition, buttons, a trackball, a jog switch, a knob, etc. included in the control panel 1650 may be provided on the main display 1210 or sub display 1220 in the form of a GUI.

Referring to FIG. 13C, the ultrasound imaging apparatus 1000c may be implemented as a portable type apparatus. Examples of the portable ultrasound imaging apparatus 1000c may include, but are not limited to, a smart phone including a probe and an application, a laptop computer, a PDA, and a tablet PC.

The ultrasound imaging apparatus 1000c may include a probe 900 and a main body 1430, and the probe 900 may be connected to one side of the main body 1430 by wire or wirelessly. The main body 1430 may include a touch screen 1450 for displaying an ultrasound image, various pieces of information processed by the ultrasound imaging apparatus 1000c, a GUI, etc.

Embodiments may be implemented through non-transitory computer-readable recording media having recorded thereon computer-executable instructions and data. Examples of the non-transitory computer-readable recording media include magnetic storage media (e.g., ROM, floppy disks, hard disks, etc.), optical recording media (e.g., CD-ROMs or DVDs), and transmission media such as Internet transmission media.

While the present disclosure has been particularly shown and described with reference to exemplary embodiments thereof, it will be understood by those of ordinary skill in the art that various changes in form and details may be made therein without departing from the spirit and scope of the inventive concept as defined by the following claims. Accordingly, the above embodiments and all aspects thereof are examples only and are not limiting.

The instructions may be stored in the form of program codes, and when executed by a processor, generate a predetermined program module to perform a specific operation.

Furthermore, when being executed by the processor, the instructions may perform specific operations according to the embodiments.

While one or more embodiments have been described with reference to the figures, it will be understood by those of ordinary skill in the art that various changes in form and details may be made therein without departing from the spirit and scope of the present disclosure as defined by the following claims. Accordingly, the above embodiments and all aspects thereof are examples only and are not limiting.

What is claimed is:

1. An ultrasound imaging apparatus configured to generate an ultrasound Doppler image of a region of an interest (ROI) of an object, the ultrasound imaging apparatus comprising:
an ultrasound probe comprising a plurality of transducers that are configured to convert electric signals into ultrasound signals or ultrasound signals into electric signals, wherein the ultrasound probe is configured to transmit ultrasound signals to the object at intervals of a pulse repetition frequency (PRF), receive ultrasound echo signals reflected from the object, and acquire a first ensemble number of ensemble data by focusing and demodulating the ultrasound echo signals;
a memory configured to store the acquired first ensemble number of ensemble data;
a processor configured to:
selectively extract a second ensemble number of ensemble data from among the stored first ensemble number of ensemble data to thereby generate a plurality of ensemble data sets,
perform clutter filtering on the ensemble data in the plurality of ensemble data sets,
calculate power components and velocity components of the ensemble data in the plurality of ensemble data sets that have been clutter filtered, and
generate a plurality of frames of color Doppler mode images respectively based on the calculated power components and velocity components of the ensemble data in the plurality of ensemble data sets; and
a display configured to display the plurality of frames of color Doppler mode images,
wherein the processor is further configured to selectively extract the second ensemble number of ensemble data from among the first ensemble number of ensemble data stored in the memory by sequentially extracting the second ensemble number of ensemble data in an overlapping manner, skipping at least one ensemble data.

2. The ultrasound imaging apparatus of claim 1, wherein the second ensemble number is less than or equal to the first ensemble number.

3. The ultrasound imaging apparatus of claim 1, wherein the second ensemble number is greater than or equal to two (2).

4. The ultrasound imaging apparatus of claim 1, wherein the processor is further configured to select and extract each of the stored first ensemble number of ensemble data at least once.

5. The ultrasound imaging apparatus of claim 1,
wherein the ensemble data comprise In-phase-Quadrature (IQ) data.

6. The ultrasound imaging apparatus of claim 1, wherein the ultrasound probe is further configured to acquire radio frequency (RF) data from the ultrasound echo signals, and wherein the processor is further configured to generate a single frame of a brightness (B) mode image based on the RF data.

7. The ultrasound imaging apparatus of claim 1, wherein the processor is further configured to arrange the generated plurality of frames of color Doppler mode images at equally spaced intervals along a time axis, and
wherein each interval is equal to a frame rate at which each of the plurality of frames of color Doppler mode images is displayed on the display.

8. A method of generating an ultrasound Doppler image of a region of an interest (ROI) of an object, the method comprising:
transmitting ultrasound signals to the object at intervals of a pulse repetition frequency (PRF), receiving ultrasound echo signals reflected from the object, and acquiring a first ensemble number of ensemble data by focusing and demodulating the ultrasound echo signals;
storing the acquired first ensemble number of ensemble data;
selectively extracting a second ensemble number of ensemble data from among the stored first ensemble number of ensemble data and generating a plurality of ensemble data sets;
performing, after the generating of the plurality of ensemble data sets, clutter filtering on the ensemble data in the plurality of ensemble data sets;
calculating velocity components and power components of the ensemble data in the plurality of ensemble data sets that have been clutter filtered; and
generating a plurality of frames of color Doppler mode images respectively based on the calculated power components and velocity components of the ensemble data in the plurality of ensemble data sets,
wherein the selectively extracting comprises sequentially extracting the second ensemble number of ensemble data from among the stored first ensemble number of ensemble data in an overlapping manner, skipping at least one ensemble data.

9. The method of claim 8, wherein the second ensemble number is less than or equal to the first ensemble number.

10. The method of claim 8, wherein the second ensemble number is greater than or equal to two (2).

11. The method of claim 8, wherein each of the stored first ensemble number of ensemble data is selected and extracted at least once.

12. The method of claim 8,
wherein the ensemble data comprise In-phase-Quadrature (IQ) data.

13. The method of claim 8, further comprising:
acquiring radio frequency (RF) data from the ultrasound echo signals; and
generating a single frame of a brightness (B) mode image based on the RF data.

14. The method of claim 8, further comprising:
arranging the generated plurality of frames of color Doppler mode images at equally spaced intervals along a time axis so that each interval is equal to a frame rate at which each of the plurality of frames of color Doppler mode images is displayed on a display; and
displaying the plurality of frames of color Doppler mode images on the display.

15. A non-transitory computer-readable recording medium having recorded thereon a program for causing an ultrasound imaging apparatus to perform a method for generating an ultrasound Doppler image of a region of an interest (ROI) of an object, the method comprising:

transmitting ultrasound signals to the object at intervals of a pulse repetition frequency (PRF), receiving ultrasound echo signals reflected front the object, and acquiring a first ensemble number of ensemble data by focusing and demodulating the ultrasound echo signals;

storing the acquired first ensemble number of ensemble data;

selectively extracting a second ensemble number of ensemble data from among the stored first ensemble number of ensemble data and generating a plurality of ensemble data sets;

performing, after the generating of the plurality of ensemble data sets, clutter filtering on the ensemble data in the plurality of ensemble data sets;

calculating velocity components and power components of the ensemble data in the plurality of ensemble data sets that have been clutter filtered; and generating a plurality of frames of color Doppler mode images respectively based on the calculated power components and velocity components of the ensemble data in the plurality of ensemble data sets, wherein the selectively extracting comprises sequentially extracting the second ensemble number of ensemble data from among the stored first ensemble number of ensemble data in an overlapping manner, skipping at least one ensemble data.

\* \* \* \* \*